(12) United States Patent
Fermon et al.

(10) Patent No.: US 8,063,631 B2
(45) Date of Patent: Nov. 22, 2011

(54) METHOD AND DEVICE FOR NON DESTRUCTIVE EVALUATION OF DEFECTS IN A METALLIC OBJECT

(75) Inventors: Claude Fermon, Orsay (FR); Myriam Pannetier, Bures sur Yvette (FR); Nicolas Biziere, Rozay en Brie (FR); Francois Vacher, Toulouse (FR); Thierry Sollier, Antony (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 497 days.

(21) Appl. No.: 12/280,414

(22) PCT Filed: Feb. 24, 2006

(86) PCT No.: PCT/EP2006/002599
§ 371 (c)(1),
(2), (4) Date: Apr. 9, 2009

(87) PCT Pub. No.: WO2007/095971
PCT Pub. Date: Aug. 30, 2007

(65) Prior Publication Data
US 2009/0206831 A1 Aug. 20, 2009

(51) Int. Cl.
*G01N 27/82* (2006.01)
*G01R 33/09* (2006.01)
(52) U.S. Cl. .................. 324/235; 324/238; 324/240
(58) Field of Classification Search ............. 324/235
See application file for complete search history.

(56) References Cited

U.S. PATENT DOCUMENTS
6,504,363 B1 * 1/2003 Dogaru et al. .............. 324/235
(Continued)

FOREIGN PATENT DOCUMENTS
DE 41 29 259 A1 3/1993
(Continued)

OTHER PUBLICATIONS

Pannetier M. et al.: "Noise in small magnetic systems—applications to very sensitive magnetoresistive sensors," Journal of Magnetism and Magnetic Materials, Elsevier Science Publishers, Amsterdam NL, vol. 290-291 (Apr. 2005), pp. 1158-1160.
Jeng et al.: "Depth-resolved eddy-current detection with GMR magnetometer," Journal of Magnetism and Magnetic Materials, Elsevier Science Publishers, Amsterdam NL, vol. 304, No. 1 (Sep. 2006) pp. e470-e473.

(Continued)

*Primary Examiner* — Jay Patidar
(74) *Attorney, Agent, or Firm* — Weingarten, Schurgin, Gagnebin & Lebovici LLP

(57) ABSTRACT

A device for non destructive evaluation of defects in a metallic object (2) by eddy currents, comprises a field emitter (3) for emitting an alternating electromagnetic field at a first frequency fi in the neighborhood of the metallic object (2), and a magnetoresistive sensor (1) for detecting a response signal constituted by a return electromagnetic field which is re-emitted by eddy currents induced by the alternating electromagnetic field in the metallic object (2). The device further comprises: a driving circuit (230) for driving the magnetoresistive sensor (1) by a current at a second frequency fc which is different from the first frequency fi, so that the magnetoresistive sensor (1) acts as an in situ modulator; a detector for detecting a response signal between the terminals of the magnetoresistive sensor (1); a filter for filtering the response signal detected by the magnetoresistive sensor (1) to keep either the frequency sum (fi+fc) of the first and second frequencies or the frequency difference (fi−fc) of the first and second frequencies, and a processor for processing the filtered response signal and extract eddy current information on defects in the metallic object (2).

33 Claims, 6 Drawing Sheets

U.S. PATENT DOCUMENTS

| | | | |
|---|---|---|---|
| 6,586,930 B1 | 7/2003 | Kumar et al. | |
| 6,693,425 B2 | 2/2004 | Wache | |
| 6,888,346 B2 * | 5/2005 | Wincheski et al. | 324/235 |
| 7,012,425 B2 * | 3/2006 | Shoji | 324/240 |
| 2005/0062470 A1 | 3/2005 | Shoji | |
| 2005/0140355 A1 | 6/2005 | Yamada et al. | |

FOREIGN PATENT DOCUMENTS

| | | |
|---|---|---|
| WO | WO 2005/114243 A2 | 12/2005 |

OTHER PUBLICATIONS

Fermon C. et al.: "Optimised GMR sensors for low and high frequencies applications," Sensors and Actuators A [Online] vol. 129 (Jan. 20, 2006), pp. 203-206. Retrieved from the Internet: URL:www.sciencedirect.com> [retrieved on Oct. 10, 2006].

International Search Report dated Nov. 13, 2006, issued in PCT/EP2006/002599.

* cited by examiner

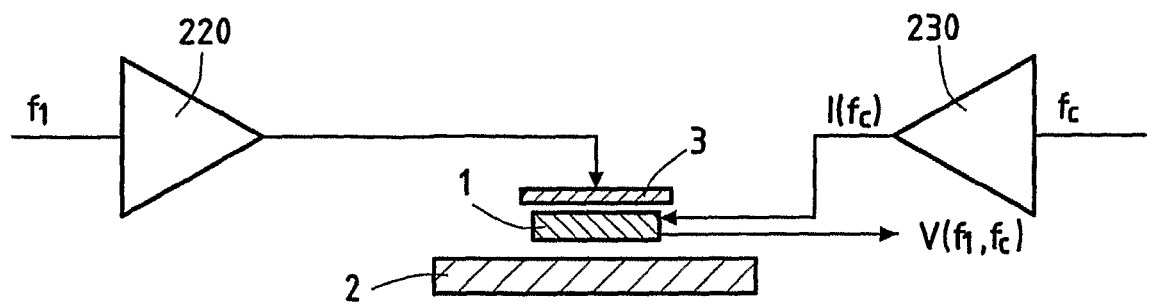
FIG.1
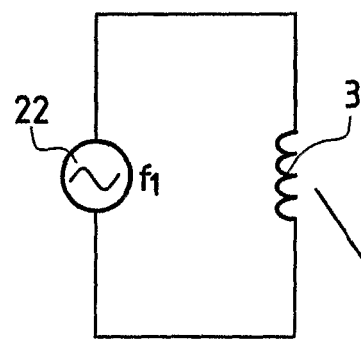
FIG.2
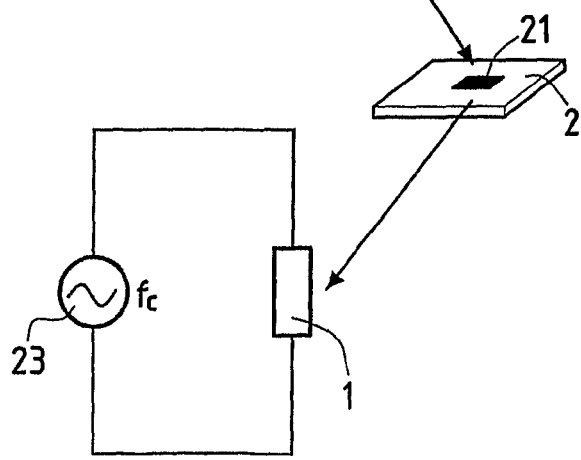

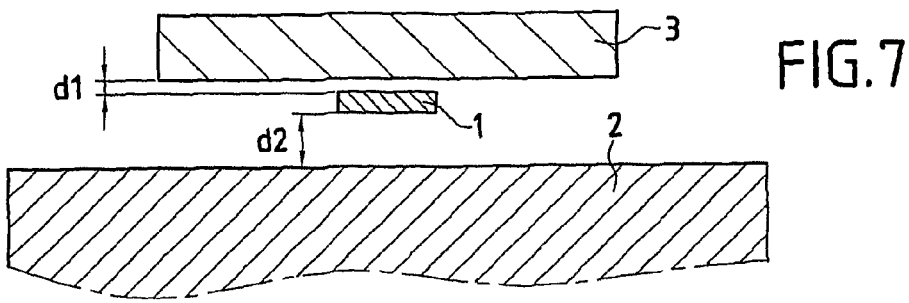
FIG.7
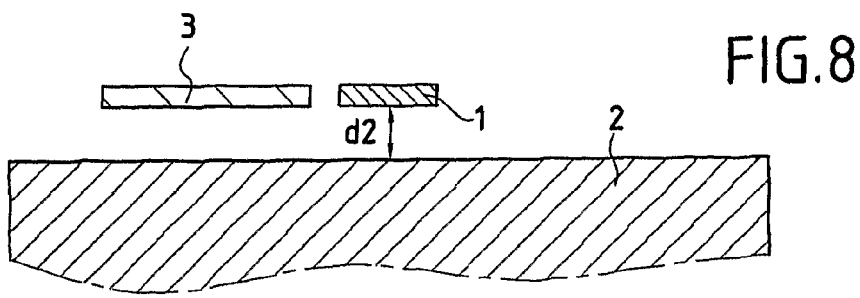
FIG.8
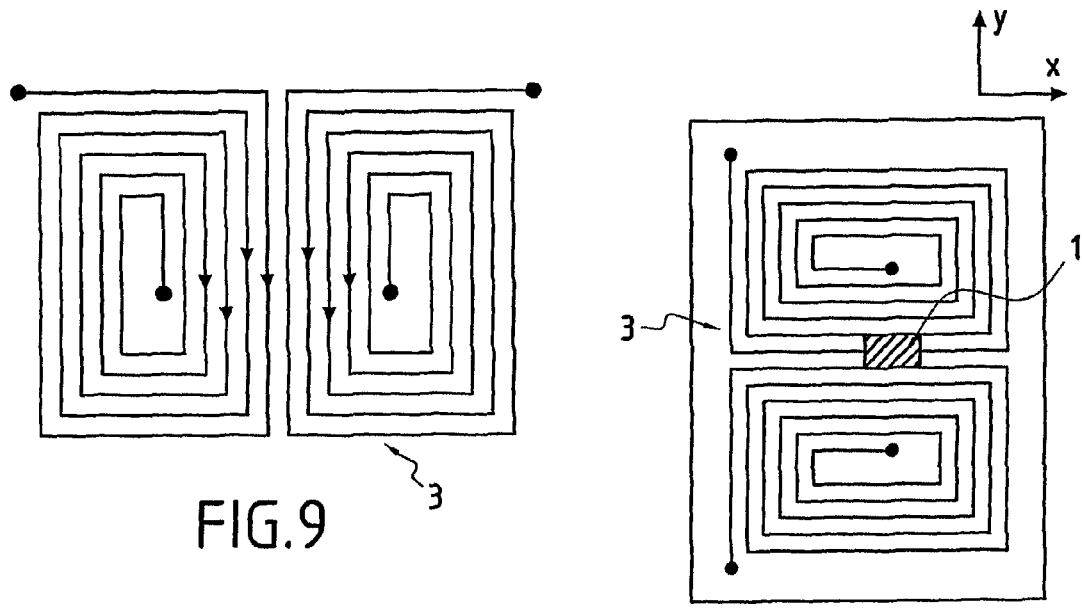
FIG.9
FIG.10
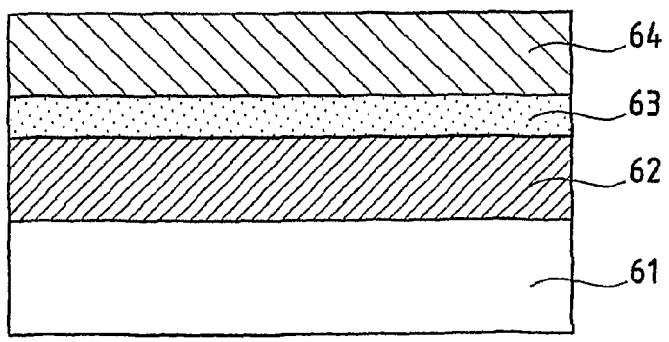
FIG.11

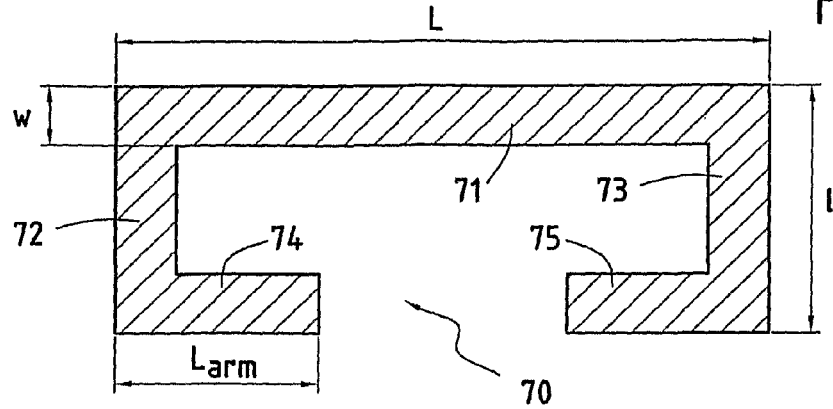
FIG.12
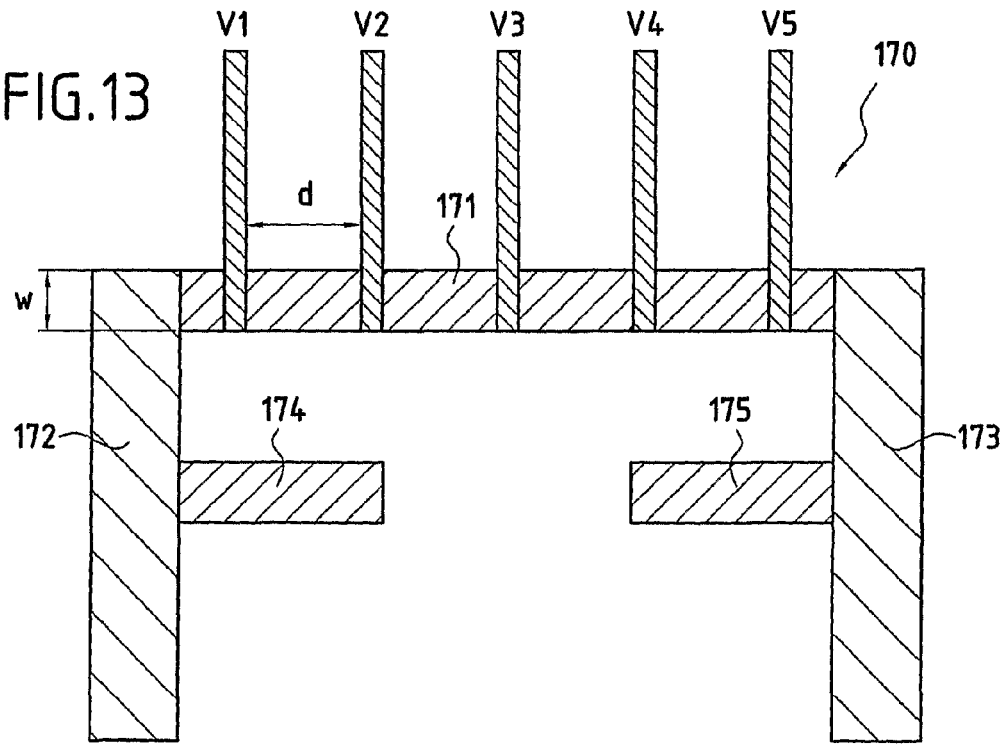
FIG.13
FIG.17
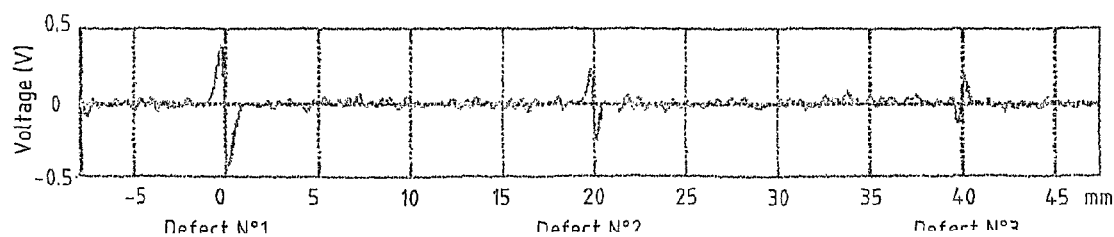

US 8,063,631 B2

METHOD AND DEVICE FOR NON DESTRUCTIVE EVALUATION OF DEFECTS IN A METALLIC OBJECT

This application is a §371 national phase filing of PCT/EP2006/002599 filed Feb. 24, 2006.

BACKGROUND OF THE INVENTION

1. Field of the Invention

The present invention relates to a method and a device for non destructive evaluation of defects in a metallic object by eddy currents.

The invention more specifically relates to a method for non destructive evaluation of defects in a metallic object by eddy currents, the method comprising the steps of emitting at least one alternating electromagnetic field at at least one first frequency fi in the neighbourhood of the metallic object and detecting through at least one magnetoresistive sensor a response signal constituted by a return electromagnetic field which is re-emitted by eddy currents induced by the alternating electromagnetic field in said metallic object.

2. Description of the Related Art

The technique of detection of defects in metallic objects by observation of the deformation of eddy currents lines has been well known and widely used for a long time.

The principle is to use an electromagnetic field emitter in the neighbourhood of the metallic object for creating eddy currents in this object. These eddy currents retransmit a radiofrequency field which can be detected by a receiver. In case of a presence of a defect, the current lines are perturbed and the electromagnetic field which is reemitted is modified in its amplitude and its phase distribution but its frequency remains unchanged.

Classical approaches use inductive coils as emitter of a radiofrequency field and as receiver of the re-emitted radiofrequency field.

More recently, the use of other kinds of sensors, like magneto-resistive sensors, has been proposed for the receiver part. Magneto-resistive elements (MREs) based on the so called "giant magnetoresistive effect" (GMR effect) have been demonstrated, for example in spin valves consisting of two adjacent magnetic layers, whose resistance R varies as a function of the applied magnetic field. In these GMR devices, variations of resistance $\Delta R_{max}$ have been observed with $\Delta R_{max}/R$-values as large as 15%.

Some patents and publications show magneto-resistive sensors applied for eddy current (EC) testing.

For instance, in the document US2005/0140355 A1, a specific embodiment of the excitation coil on a printed circuit board (PCB) is used and a magnetoresistive (MR) sensor is located on the opposite side of the PCB to detect the magnetic field related to the eddy currents modified by a defect.

In the document US2005/0062470 A1, an eddy current probe having a non planar form allows the displacement of the probe in a close proximity to the object's surface avoiding an adsorption phenomenon due to static friction.

In these documents, the designs of the excitation loop and the sensor are addressed to improve the detection.

In the document U.S. Pat. No. 6,693,425 B2, the excitation current in the coil varies to obtain a varying field penetrating in the component under test. This invention allows scanning defects of varying depths.

In all these cases, even if the sensitivity is increased, the sensor which might be either a coil or a magnetoresistive element, detects the signal of the eddy current at a frequency equal to the excitation coil's frequency, and is therefore limited in term of signal-to-noise ratio.

SUMMARY OF THE INVENTION

The present invention aims at overcoming the shortcomings and drawbacks of the methods and devices of the prior art.

More specifically a main object of the present invention is to increase the signal-to-noise ratio and to get rid of the main fluctuations of sensors due for example to the temperature drift or to ageing.

These aims are achieved due to a method for non destructive evaluation of defects in a metallic object by eddy currents, the method comprising the steps of emitting at least one alternating electromagnetic field at at least one first frequency fi in the neighbourhood of the metallic object and detecting through at least one magnetoresistive sensor a response signal constituted by a return electromagnetic field which is re-emitted by eddy currents induced by the alternating electromagnetic field in said metallic object, characterized in that it comprises the further steps of driving said at least one magnetoresistive sensor by a current at a second frequency fc which is different from said first frequency fi, so that said at least one magnetoresistive sensor acts as an in situ modulator and filtering the response signal detected by said at least one magnetoresistive sensor to keep either the frequency sum of said first and second frequencies or the frequency difference of said first and second frequencies before processing said response signal to extract eddy current information on defects in said metallic object.

The signal due to the eddy current is unambiguously different from the excitation signal and can therefore be highly amplified, thus increasing the signal-to-noise ratio.

A main advantage of the method according to the invention lies in the fact that it is possible to get rid of the main fluctuations of the magnetoresistive sensor due for example to the temperature drift or to the ageing. Furthermore, a lot of noise due to the electromagnetic interference (EMI) at the field emitter frequency may be avoided. This interference is due to the field induced by the emitter and preferentially appears for frequencies greater than 100 kHz.

According to a preferred embodiment, the filtering step comprises filtering the response signal detected by said at least one magnetoresistive sensor to keep the frequency difference of said first and second frequencies before processing said response signal to extract eddy current information on defects in said metallic object.

In such an embodiment, the alternating electromagnetic field is preferably emitted at a single first frequency f1 which is higher than 100 kHz.

According to a specific embodiment, the method comprises the steps of amplifying a voltage between first and second terminals of said magnetoresistive sensor, to obtain an amplified voltage and sending said amplified voltage to a signal input of a mixing and filtering system and mixing a frequency reference signal at said second frequency fc with a frequency reference signal at said first frequency f1 in a multiplier to obtain a product reference signal f1−fc which is applied to a reference input of the same mixing and filtering system whose output is processed as an ordinary output signal of an eddy current testing method.

This at least one magnetoresistive sensor has a sensing axis which may be placed either orthogonally or parallely to the emitted alternating electromagnetic field.

According to a particular embodiment, the response signal is detected through an array of sensors which are used as in-situ demodulators and are able to detect the different components of the return electromagnetic field which are due to the modification of the eddy currents by a defect.

According to a specific embodiment, the at least one alternating electromagnetic field is emitted in the neighbourhood of the metallic object at a set of different first frequencies which are all different from said second frequency fc.

In such a case, advantageously, the filtering step comprises filtering the response signal detected by said at least one magnetoresistive sensor to keep the frequency differences of said first and second frequencies before processing said response signal as a simple demodulated signal giving the useful signal created by the modification of the eddy currents by a defect.

According to another specific embodiment of the method according to the invention, the at least one magnetoresistive sensor has a non linear behaviour and the response signal detected by said at least one magnetoresistive sensor is filtered to keep either the frequency sum of said first frequency and n times the second frequency or the frequency difference of said first frequency and n times the second frequency, where n is an integer, before processing said response signal to extract eddy current information or defects in said metallic object.

The invention further relates to a device for non destructive evaluation of defects in a metallic object by eddy currents, comprising at least one field emitter for emitting at least one alternating electromagnetic field at at least one first frequency fi in the neighbourhood of the metallic object, and at least one magnetoresistive sensor for detecting a response signal constituted by a return electromagnetic field which is re-emitted by eddy currents induced by the alternating electromagnetic field in said metallic object, characterized in that it further comprises:

driving means for driving said at least one magnetoresistive sensor by a current at a second frequency fc which is different from said first frequency fi, so that said at least one magnetoresistive sensor acts as an in situ modulator, detecting means for detecting between the terminals of the magnetoresistive sensor a response signal, filtering means for filtering the response signal detected by said at least one magnetoresistive sensor to keep either the frequency sum of said first and second frequencies or the frequency difference of said first and second frequencies, and processing means for processing said filtered response signal and extract eddy current information on defects in said metallic object.

According to a particular embodiment, the detecting means comprises amplification means for detecting reference signals at said at least one first frequency fi and at said second frequency fc, multiplying means for mixing said at least one first frequency fi and said second frequency fc and at least a lock-in amplifier for detecting the frequency sum of said first and second frequencies or the frequency difference of said first and second frequencies.

The magnetoresistive sensor may comprise multiple contact points for voltage measurements or an array of sensors.

The magnetoresistive sensor may be a Hall effect sensor or else an anisotropic magnetoresistive sensor (AMR), a giant magnetoresistive sensor (GMR), a giant magnetoimpedance sensor (GMI) or a tunnel magnetoresistive sensor (TMR).

The magnetoresistive sensor may be constituted by any element having a resistance presenting a variation as a function of an applied external field.

The magnetoresistive sensor may be built on different kinds of substrates, e.g. a very thin silicon substrate, a bevelled substrate or a flexible substrate.

According to a specific embodiment, the magnetoresistive sensor has a yoke shape, the length of the yoke and the length of the lateral arms of the yoke each are at least three times the width of the yoke, and the width of the yoke is comprised between 2 µm and 12 µm.

Advantageously, the at least one field emitter is a planar coil.

BRIEF DESCRIPTION OF THE DRAWINGS

Other features and advantages of the invention will appear more readily from the following description of several embodiments of the present invention, given as examples, with reference to the enclosed drawings, on which:

FIG. 1 is a block diagram illustrating the main components of a device according to the present invention, FIGS. 2 to 6 diagrammatically show different embodiments of a device for implementing the present invention, FIG. 7 is a schematic cross-section of the main components used for a non destructive control by eddy currents according to a first specific embodiment, FIG. 8 is a schematic cross-section of the main components used for a non destructive control by eddy currents according to a second specific embodiment, with a sensor placed in the plane of a field emitter, FIG. 9 is a schematic drawing of a specific emitter comprising two coils which can be used in a device according to the invention, FIG. 10 shows a specific configuration with the relative positions of a field emitter and a sensor which may be implemented according to the invention, FIG. 11 is a schematic cross-section of a GMR or TMR stack in a spin valve configuration, FIG. 12 shows an example of yoke-shape GMR sensor which may be used in a device according to the invention, FIG. 13 shows another example of GMR sensor which comprises multiple channel output, FIG. 17 is a diagram showing the responses obtained on a GMR sensor when scanning three defects in an inconel plate.

DETAILED DESCRIPTION OF PREFERRED EMBODIMENTS

Figure 3:
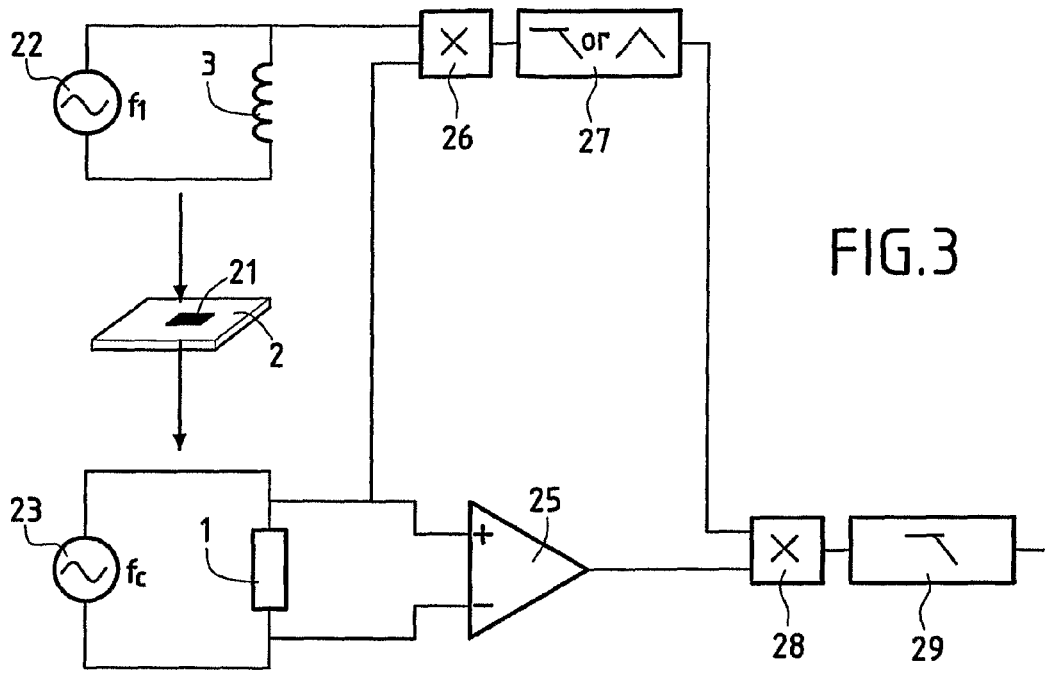

The invention essentially addresses a method which improves the signal-to-noise ratio of the detection of defects through measurement of eddy currents, by using a magnetoresistive sensor as an in situ demodulator.

The principle of the measurement method will be explained hereafter with reference to FIG. 1.

An emitter 3, which can be a coil for instance, is fed through an amplifier 220 with an alternating current (AC) or radiofrequency (RF) field at a frequency f1. The emitter 3, which is located in close proximity to a metallic object 2 to be inspected, sends in turn the AC or RF field at the frequency f1 in the tested object 2. The object to be inspected 2 re-emits a signal at the frequency f1.

According to the invention a magnetoresistive (MR) sensor 1 is located in the vicinity of the object to be inspected 2 and is fed through an amplifier 230 with a radiofrequency current at a frequency fc which is different from the working frequency f1.

The MR sensor 1 is thus used as an in situ mixer.

The voltage V measured at the active points of the MR element is then given by:

$$V=RI=(R_0+R_1H\cos(2\pi f_1 t+\phi_H)+\ldots)*I_0\cos(2\pi f_c t) \quad (1)$$

which can be developed as:

$$V=RI=R_0 I_0 \cos(2\pi f_c t)+(R_1 H I_0 \cos(2\pi (f_1-f_c)t+\phi_H)+ \\ R_1 I_0 H \cos(2\pi (f_1+f_c)t+\phi_H)+R_n H^n I_0 \cos^n(2\pi (f_1-f_c) \\ t+\phi_H)+R_n H^n I_0 \cos^n(2\pi (f_1+f_c)t+\phi_H)$$

This development shows that the two first terms depending on the sum and difference of the frequencies are exactly proportional to H. H is the total field experienced by the sensor, i.e. the vectorial sum of the emitting field by the coil 3 and the field reemitted by the eddy current. The higher order terms ($n \geq 2$) depend on frequencies different from the sum and the difference and may be rejected by adequate filtering. Usually a sensor is sensitive to only one direction of field and then the value of H is the projection of the total field along that axis.

The main advantages of that approach are first to get rid of the fluctuations of the resistance $R_0$ due for example to the temperature or the ageing. Finally, non linearity of the MR sensors does not affect the result. The non linearity of a sensor gives the appearance of terms $R_n$ which have a frequency of $f_1-nf_c$ and $f_1+nf_c$ different from the measured frequency and which can then easily be eliminated if the frequencies are chosen different enough.

Secondly, this principle of measurement avoids a lot of noise effects due to the electromagnetic interference (EMI) at the field emitter frequency. This interference is due to field induced by the emitter 3 and preferentially appears for frequencies greater than 100 kHz. EMI can be induced by the coupling between the field emitter 3 and the parasitic connection loops or the coupling between the field emitter 3 and unshielded tracks. At frequency f1 comparable or larger than 10 MHz, it is indeed quite impossible to avoid disturbing signals due to the connection loops.

The principle of the method according to the present invention will be more clearly described with reference to the examples of FIGS. 2 to 6.

Figure 4:
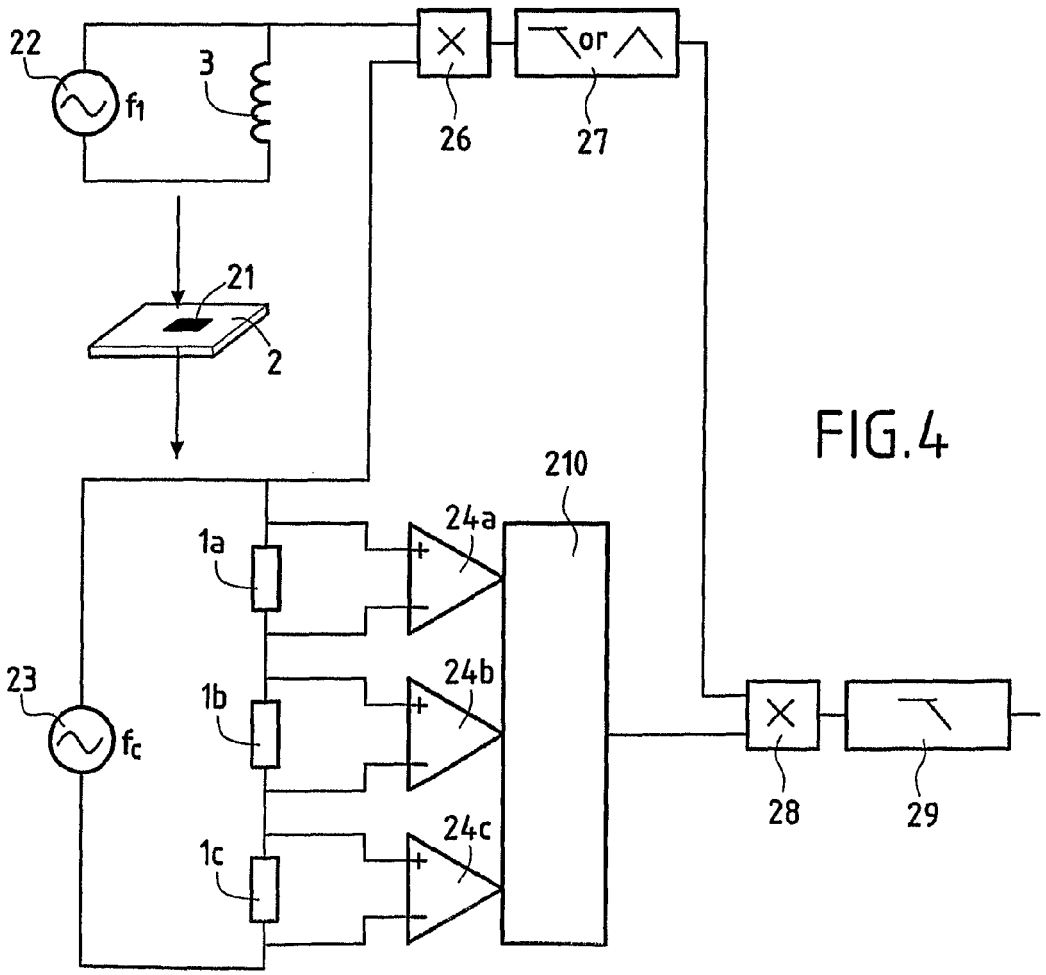

An emitter coil 3 is fed by a waveform generator 22 at the frequency f1 (FIGS. 2 to 4).

A magnetic field is produced by the coil 3 in the vicinity of a metallic piece 2. This magnetic field is modified by the presence of a defect 21 in the metallic piece 2 to be controlled.

A magnetoresistive sensor 1, which is powered by a generator 23 at the frequency fc, measures the magnetic field which has been modified by the presence of the defect 21.

FIG. 3 illustrates an embodiment of the acquisition system. The voltage across the sensor 1 is measured by a differential amplifier 25. The frequency of the signal outputted by the differential amplifier 25 can be |f1−fc| or f1+fc.

The signals outputted by the waveform generators 22 and 23 are mixed in a mixer 26 to form a reference signal. A filter 27 is connected at the output of the mixer 26. The filter 27 is a low pass filter if a reference signal is selected to be at the frequency |f1−fc| and is a bandpass filter if a reference signal is selected to be at the frequency f1+fc.

A mixer 28 and a filter 29 constitute a lock-in amplifier for receiving on the one hand the output of the differential amplifier 25 and on the other hand the reference signal outputted by the filter 27.

The filter 29 is a low pass filter.

FIG. 4 shows an example of acquisition system when the magnetoresistive sensor 1 comprises an array of several magnetic sensors 1a, 1b, 1c which are connected in series. In such a case, several differential amplifiers 24a, 24b, 24c are used to measure the voltages of each of the individual sensors 1a, 1b, 1c respectively. A multiplexer 210 selects one of the voltages outputted by the differential amplifiers 24a, 24b, 24c. This selected voltage is then applied to a mixer 28 of a common lock-in amplifier 28, 29 in a manner similar to the embodiment of FIG. 3.

Since the same sensing current is used for all different individual magnetic sensors 1a, 1b, 1c, the overall system may remain simple and only one lock in amplifier 28, 29 is necessary.

The present invention may be in principle implemented with working frequencies varying from DC to GHz frequencies. However, in practice the working frequency fi should be chosen as a function of the type of the investigated defects.

For example, defects of the order of 100 μm should be preferably detected with frequencies fi ranging from 1 MHz to 20 MHz. The signal can be detected at a frequency fc which is substantially different from the working frequency fi. For example, a working frequency fi might be 5 MHz whereas the corresponding frequency fc is 5.1 MHz.

The signal can thus be detected at low frequency (e.g. under 100 kHz) using the difference fi−fc to allow an easy amplification.

However, the signal can also be detected at high frequency, using the sum fi+fc (e.g. 10.1 MHz) to allow an easier filtering and noise suppression.

The detection of defects which are larger than 100 μm requires working frequencies fi preferably lower than 1 Mhz.

The invention may be implemented with a single working frequency f1 as disclosed with reference to FIGS. 1 to 4.

However alternatively a set of several frequencies fi can be sent by the field emitter 3. A frequency fc which is different from the working frequencies fi is applied to the magnetoresistive sensor 1 and then a set of frequencies |fi−fc| are detected at the output of the sensor 1.

Figure 5:
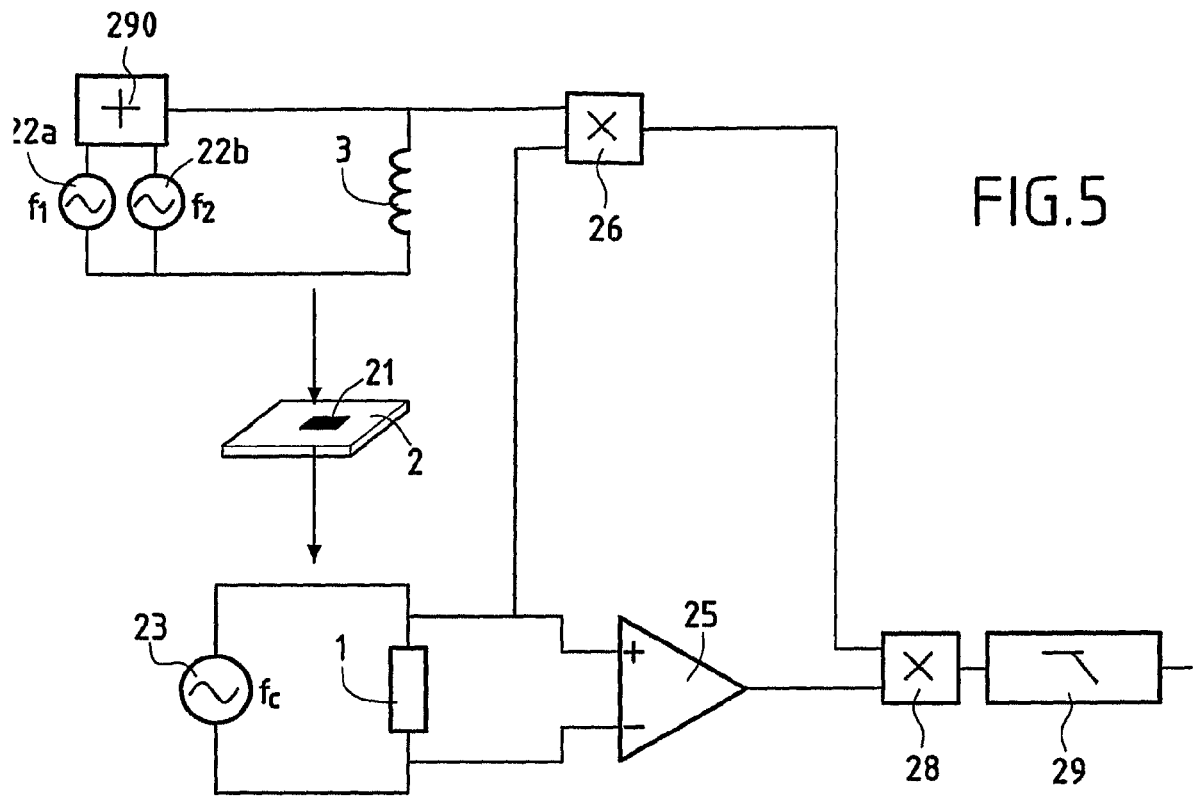

FIG. 5 illustrate a possible embodiment using a set of two working frequencies f1 and f2 which are produced by waveform generators 22a, 22b respectively and are applied to an adder 290 whose output is connected to an emitter coil 3. The magnetoresistive sensor 1 is fed at a frequency fc by a waveform generator 23 in the same manner as in the embodiment of FIG. 3. The voltage across the sensor 1 is measured by a differential amplifier 25.

The sum of frequencies f1 and f2 outputted by the adder 290 and the frequency fc are mixed in a mixer 26 which outputs a reference signal which is applied to a first input of a mixer 28 of a lock-in amplifier 28, 29.

The output of the differential amplifier 25 is applied to a second input of the mixer 28 which is associated with a low pass filter 29 for measuring the useful signals |f1−fc| and |f2−fc| which will then permit to detect the defects 21 of the metallic piece 2 simultaneously at different working frequencies.

Figure 6:
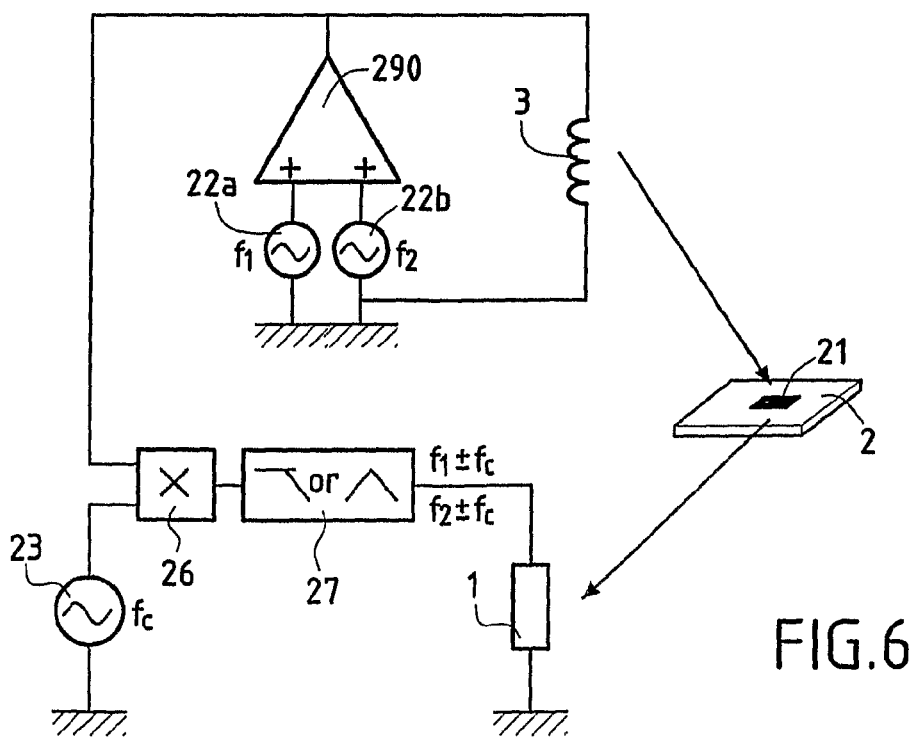

FIG. 6 shows an example of another possible embodiment using two different working frequencies f1, f2.

A set of working frequencies f1, f2 generated by waveform generators 22a, 22b respectively are applied to the inputs of an adder 290. The output of the adder 290 is connected to an emitter coil 3 and to a first input (reference input) of a mixer 26.

A frequency fc generated by a waveform generator 23 is applied to a second input of the mixer 26.

The output of the mixer 26 is applied to a filter 27 which is connected to a magnetoresistive sensor 1.

The filter 27 is a low pass filter for outputting signals f1−fc and f2−fc or a bandpass filter for outputting signals f1+fc and f2+fc.

The output voltage of the sensor 1 may be analyzed with a lock in amplifier or a bandpass filter at the frequency fc in a manner similar to the embodiment of FIG. 5. The signals which are provided by the magnetic field emitted by the coil 3 at several frequencies f1, f2 are demodulated at the same frequency fc which is different from f1 and f2.

It might also be possible to use a magnetoresistive sensor 1 having a non linear behaviour, such as a sensor including a TMR junction. In such a case, the equation giving the voltage V measured at the active points of the magnetoresistive element comprises terms $R_n$ (e.g. $R_2$) which have a frequency of fi−$nf_c$ and fi+$nf_c$ where n is an integer such as 2. These frequencies fi−$nf_c$ and fi+$nf_c$ can be filtered and the detection may thus be done at |fi−$nf_c$| or fi+$nf_c$.

FIG. 7 shows a typical configuration of a device for a non destructive control by eddy currents.

The field emitter 1 is placed in the vicinity of the surface of an element 2 to be explored, at a distance $d_2$ thereof. The sensor 3 is placed near the field emitter 1, at a small distance $d_1$ thereof. The field emitter 1 is thus located in the gap between the sensor 3 and the metallic object 2.

Preferably, the distance $d_1$ between the field emitter 1 and the sensor 3 is well determined and is fixed. The system comprising the field emitter 1 and the sensor 3 may be designed to move along the main surface of the object 2. During this scanning operation the distance $d_2$ between the object 2 and the emitter 1 secured to the sensor 3 may slightly vary.

FIG. 8 shows an alternative configuration of a device according to the invention. The sensor 3 is placed in the vicinity of the field emitter 1 substantially in the same plane at a distance $d_2$ from the main surface of the object 2 to be examined.

The distance $d_2$ is all the more critical as the size of the searched flaw is small.

To better characterizing the shape of a defect it is possible to measure different components of the magnetic field created by the eddy currents by using a plurality of magnetoresistive sensors 3 having different sensitive axes.

In particular at least one magnetoresistive sensor may have a sensing axis which is placed orthogonally to the emitted alternating electromagnetic field and at least one magnetoresistive sensor may have a sensing axis which is placed parallely to the emitted alternating electromagnetic field.

Different kinds of field emitters 3 may be used. For example, the field emitters 3 may comprise vertical coils, horizontal coils or planar exciting coils as described in document US2005/0140355 A1. The shape of the field emitter 3 depends on the characteristics of the defect which is to be detected and on the shape of the piece under test. The field emitter 3 may create a field which is perpendicular to the surface of the object under test or along the plane of the surface of the object under test.

FIG. 9 shows an example of a current sheet having a plane of symmetry and which may be used to create an homogeneous field over the central part of the emitter 3.

The position of the sensor 1 is preferably chosen to cancel the direct coupling between the sensor 1 and the emitter coil 3.

FIG. 10 shows a possible embodiment where the sensor 1 is sensitive to the field along the x axis whereas the field emitter 3 creates a field along the y axis. The field which is produced by the emitter coil 3 being oriented along the y axis, there is no direct coupling between the sensor 1 and the emitter coil 3.

Alternative configurations for the field emitter 3 and the sensor 1 may be used. The configuration should be optimized as a function of the characteristics of the searched defect and of the shape of the object under test.

The MR sensor is characterized in that its resistance varies as a function of the applied field. Within various kinds of MR sensors, one may mention the Hall sensor, Anisotropic Magnetoresistance (AMR), Giant Magnetoresistance (GMR) and Tunnel Magnetoresistance (TMR) sensors. The sensor fabrication is well known. For all AMR sensors, a single layer of soft magnetic material such as permalloy can be used with a MR variation of about 2%.

For GMR sensors, a spin valve configuration (FIG. 10) is preferable to a multiple layer GMR like $(Co/Cu)_n$ or $(NiFe/Ag)_n$ in order to avoid static bias field.

A spin valve configuration as shown on FIG. 11 consists of several layers deposited on a substrate 61 which may be typically made of silicon or glass. The spin valve comprises a hard magnetic layer 64, made of an antiferromagnetic layer coupled to a ferromagnetic layer, and a free magnetic layer 62 made of one or several ferromagnetic layers. These two stacks are separated by a thin metallic layer 63 (typically a copper layer 1-2 nm thick). Simple spin valves or spin valves with an artificial antiferromagnetic layer can be used. Typical MR variation on these systems are 10%. When replacing the metallic layer by an insulating layer, one obtains a TMR system. The MR ratio can reach 350% in these systems.

The shape of the MR sensor is essential for the signal-to-noise performance.

In case of a Hall sensor, a square or rectangular shape is well adapted for the measurement. The Hall sensor is placed so that it is sensitive to the field reemitted perpendicularly to the surface. AMR, GMR or TMR sensors are usually sensitive to in-plane fields and then will be in general used to detect the in-plane fields reemitted by the defect.

For an AMR, GMR or TMR sensor, a preferred shape is a yoke shape sensor 70 presenting a reasonable flux closure as shown on FIG. 12.

The yoke dimension should preferably be bounded by several constraints:
  the length (L) of the main part 71 of the yoke can be as long as necessary to cover the measuring zone. It can be comprised between 10 µm to several centimeters. For noise reasons, its length should be at least 3 times the width (w) of this main part 71 of the yoke;
  the length (l) of the arms 72, 73 of the yoke should be at least 3 times the width w;
  the width (w) of the yoke should be preferably comprised between 2 µm and 12 µm. The sensitivity is decreasing with the width w and the low frequency noise is increasing with the width w. A width of 10 to 12 µm is optimal. Larger widths are possible, depending on the material, but could induce less stable devices, due to magnetic domain formation. In case of TMR sensors, the free layer only needs to have a yoke shape.

The arms 72 and 73 of the yoke are linked to additional arms 74, 75 which are parallel to the main part 71 but have a length $L_{arm}$ which is comprised between about ¼ and ⅓ of the overall length L.

In all cases, a resistance between two points of measurement comprised between 50 Ohms and several kOhms can be used. In terms of signal-to-noise ratio, it is better to use a higher resistive value as the signal will be proportional to that resistance and the noise is proportional to the square root of the resistance. A four point measurement should be preferred for the improvement of signal-to-noise ratio.

The use of a bridge configuration is not necessary with the proposed method as the offset R0 is automatically suppressed by the in situ demodulation. Furthermore, a bridge configuration with only one sensitive element would add excess noise with a factor of √2.

If a rather large surface should be scanned, an array of sensors or a sensor with multiple contacts can be used. In case of an array of sensors, the same sensing current can be used for all of these.

FIG. 13 gives an example of a single sensor 170 with multiple contact points $V_1$ to $V_5$. The resolution of measurement is given by the distance d between two adjacent points.

In the case of a single sensor, the individual element is defined by the distance between two adjacent voltage contacts. In order to insure the relative independence of each element, it is then necessary, in the case of an AMR, a GMR or a TMR sensor to have a distance d between each voltage contact larger than the width w of the sensor.

The sensor 170 of FIG. 13 comprises a main part 171 and two current feeding contacts 172, 173. Arms 174, 175 close the yoke shape in a way similar to the embodiment of FIG. 12 with arms 74, 75.

MR sensors are usually deposited on silicon or on ceramics for pick up heads. For Non Destructive Evaluation (NDE) applications, silicon can be used for frequencies lower than 10 MHz due to capacitance effects which short circuit the sensor. At higher frequencies glass or insulating ceramics substrates are necessary. An alternative is to use flexible insulating substrate like the material known under the trademark Kapton.

The mechanical mounting of the sensor system is particularly important.

In order to achieve a high resolution of the detection of defects and to be able to use the small size of the MR sensor, it is necessary to optimize the design of the detecting system. In particular, the distance $d_2$ (see FIGS. 7 and 8) is all the more critical as the size of the searched flaw is small. The problem is then to be able to electrically contact the sensor as it moves over the surface.

Three preferred mechanical mountings will be described with reference to FIGS. 14 to 16. These mountings depend on the substrate chosen for the MR sensor and are intended to enhance the signal-to-noise ratio of the probe. These special mechanical mountings of the MR sensor system thus allow an optimized use of the in situ modulation.

Figure 14:
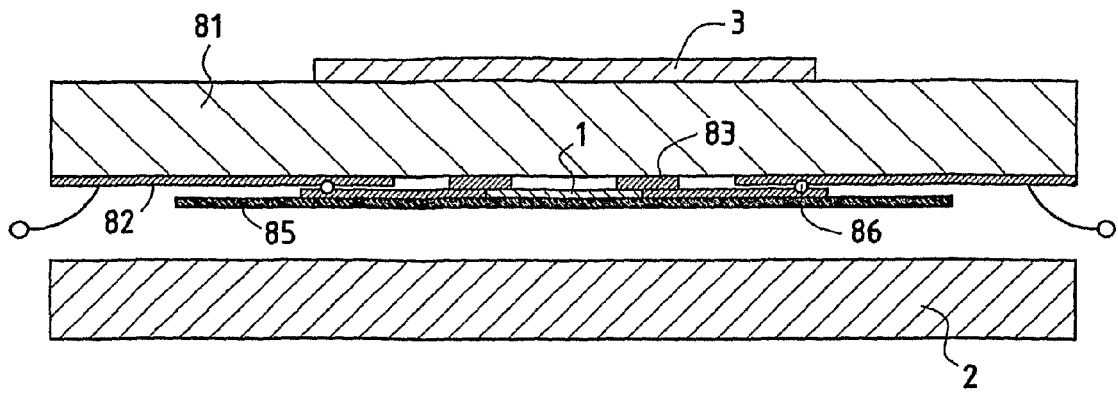
FIG. 14 is a cross-section of a specific measurement device according to the invention, where a sensor is deposited on a thin silicon substrate.

FIG. 14 shows an embodiment using a silicon substrate 85 of reduced thickness.

The sensor 1 is deposited on a silicon wafer 85 which can be as thin as possible.

The emitter 3 comprising coils for RF field emission is supported on one side of a printed circuit board (PCB) 81 which supports on its other side tracks 82, 83 for electrical contacts. The reference 82 designates deported electrical contacts for the sensors whereas reference 83 designates electrical contacts on the sensors themselves which are bonded to the PCB 81. Reference 86 designates electrical links between tracks 82 and the MR sensors 1. These electrical links may be constituted by a low fusion temperature metal such as indium which permits to solder the Si wafer 85 on the PCB 81.

The sensor is thus protected by the substrate 85 and the distance from the surface of the object 2 is given by the thickness of the substrate 85, which can be reduced down to 20 μm, when the substrate 85 is placed on the object 2 to slide along the surface to be tested.

Figure 15:
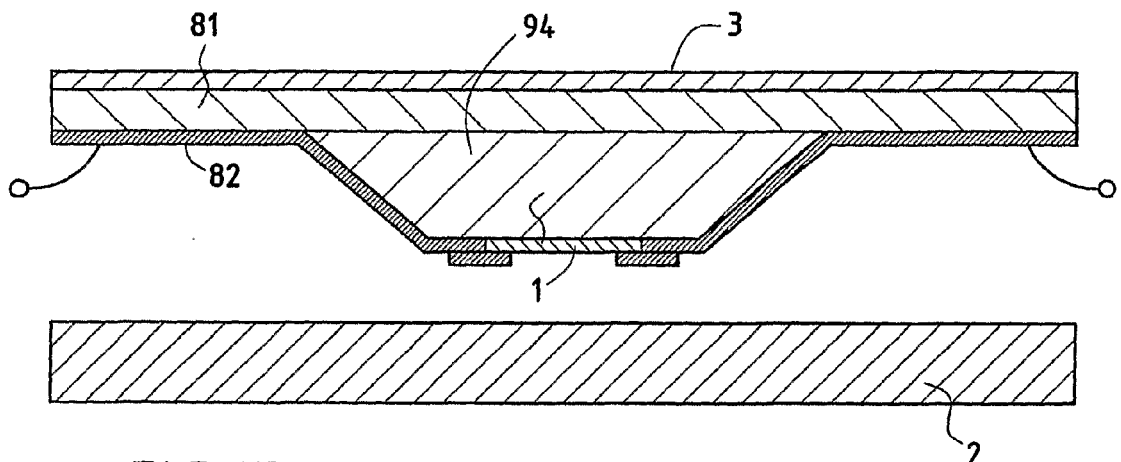
FIG. 15 is a cross-section of a specific measurement device according to the invention, where a sensor is deposited on a bevelled glass substrate.

FIG. 15 shows an alternative embodiment which uses a bevelled substrate 94.

The bevelled substrate 94 is glued on a first surface of a PCB 81 which also supports the emitter 3 (coils for RF field emission) on a second surface in a manner similar to the embodiment of FIG. 14.

The bevelled substrate 94 may be constituted by a ceramic or glass substrate. Reference numeral 82 designates deported electrical contacts for the sensors 1.

The continuity of the contacts can be maintained through the angles allowing a very small distance between the sensor 1 and the scanned object 2.

The sensor 1 can be protected either by a protective insulating layer, such as $Si_3N_4$ or $SiO_2$ or a thin Kapton™ film, allowing the protected sensor to be directly in contact with the surface of the object 2. The bevelled shape may be created by mechanical or chemical methods.

Figure 16:
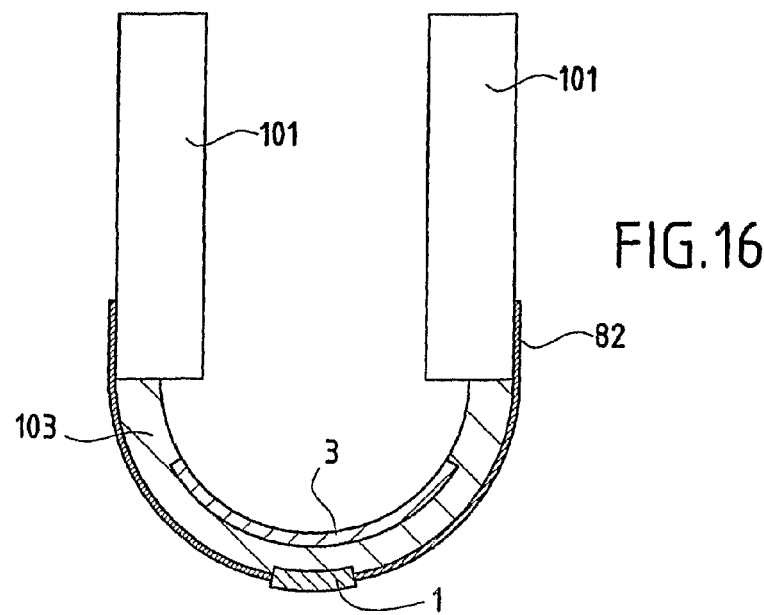
FIG. 16 is a cross-section of a specific measurement device according to the invention, where a sensor is deposited on a flexible substrate.

FIG. 16 shows another possible embodiment using a flexible substrate 103.

The substrate 103 may be constituted for example by a polyimide film known under the trademark "Kapton" of the company DUPONT. The sensor 1 and its contacts 82 are deposited on one side of the foil 103. The emitter 3 is deposited on the other side of the foil 103. The foil 103 is then bent to allow the tracks 82 to be in contact with a PCB system 101.

The results obtained with a specific embodiment used for scanning a plate having three defects of about 100 μm are given herebelow with respect to FIG. 17.

The sensing device comprises a field emitter including a double planar coil and a magnetoresistive sensor having multiple measurement points disposed on glass with bevelled edges.

The frequency f1 of the field emitter is 5 MHz and the frequency fc of the current with crosses the sensor is 5.1 MHz. The voltage V measured at the active points of the MR element is then at the frequencies f1−fc=100 kHz or f1+fc=10.1 MHz.

If a low pass filter is used, the useful signal may be measured at the frequency of f1−fc=100 kHz and it is thus possible to get rid of the disturbing signal which occurs at the frequencies f1 and fc.

The output signal shown on FIG. 17 corresponds to the detection of three defects having the following sizes:
$1^{st}$ defect: 200×100×200 μm³
$2^{nd}$ defect: 100×100×200 μm³
$3^{rd}$ defect: 100×100×100 μm³.

The invention claimed is:

1. A method for non destructive evaluation of defects in a metallic object by eddy currents, the method comprising the steps of emitting at least one alternating electromagnetic field at at least one first frequency fi in the neighbourhood of the metallic object and detecting through at least one magnetoresistive sensor a response signal constituted by a return electromagnetic field which is reemitted by eddy currents induced by the alternating electromagnetic field in said metallic object, characterized in that it comprises the further steps of driving said at least one magnetoresistive sensor by a current at a second frequency fc which is different from said first frequency fi, so that said at least one magnetoresistive sensor acts as an in situ modulator and filtering the response signal detected by said at least one magnetoresistive sensor to keep either the frequency sum (fi+fc) of said first and second frequencies or the frequency difference (fi−fc) of said first and second frequencies before processing said response signal to extract eddy current information on defects in said metallic object.

2. A method according to claim 1, characterized in that said filtering step comprises filtering the response signal detected by said at least one magnetoresistive sensor to keep the frequency difference (fi−fc) of said first and second frequencies before processing said response signal to extract eddy current information on defects in said metallic object.

3. A method according to claim 2, characterized in that the alternating electromagnetic field is emitted at a single first frequency (f1) which is higher than 100 kHz.

4. A method according to claim 3, characterized in that it comprises the steps of amplifying a voltage between first and second terminals of said magnetoresistive sensor, to obtain an amplified voltage and sending said amplified voltage to a signal input of a mixing and filtering system and mixing a frequency reference signal at said second frequency fc with a frequency reference signal at said first frequency f1 in a multiplier to obtain a product reference signal f1−fc which is applied to a reference input of the same mixing and filtering system whose output is processed as an ordinary output signal of an eddy current testing method.

5. A method according to claim 4, characterized in that the at least one magnetoresistive sensor has a sensing axis which is placed orthogonally to the emitted alternating electromagnetic field.

6. A method according to claim 4, characterized in that the at least one magnetoresistive sensor has a sensing axis which is placed parallel to the emitted alternating electromagnetic field.

7. A method according to claim 4, characterized in that the response signal is detected through an array of sensors which are used as in-situ demodulators and are able to detect the different components of the return electromagnetic field which are due to the modification of the eddy currents by a defect.

8. A method according to claim 4, characterized in that said at least one magnetoresistive sensor has a non linear behaviour and the response signal detected by said at least one magnetoresistive sensor is filtered to keep either the frequency sum (fi+nfc) of said first frequency and n times the second frequency or the frequency difference (fi−nfc) of said first frequency and n times the second frequency, where n is an integer, before processing said response signal to extract eddy current information or defects in said metallic object.

9. A method according to claim 1, characterized in that the at least one magnetoresistive sensor has a sensing axis which is placed orthogonally to the emitted alternating electromagnetic field.

10. A method according to claim 1, characterized in that the at least one magnetoresistive sensor has a sensing axis which is placed parallel to the emitted alternating electromagnetic field.

11. A method according to claim 1, characterized in that the response signal is detected through an array of sensors which are used as in-situ demodulators and to detect the different components of the return electromagnetic field which are due to the modification of the eddy currents by a defect.

12. A method according to claim 1, characterized in that said at least one alternating electromagnetic field is emitted in the neighbourhood of the metallic object at a set of different first frequencies (f1, f2) which are all different from said second frequency fc.

13. A method according to claim 12, characterized in that said filtering step comprises filtering the response signal detected by said at least one magnetoresistive sensor to keep the frequency differences (f1−fc, f2−fc) of said first and second frequencies before processing said response signal as a simple demodulated signal giving the useful signal created by the modification of the eddy currents by a defect.

14. A method according to claim 1, characterized in that said at least one magnetoresistive sensor has a non linear behaviour and the response signal detected by said at least one magnetoresistive sensor is filtered to keep either the frequency sum (fi+nfc) of said first frequency and n times the second frequency or the frequency difference (fi−nfc) of said first frequency and n times the second frequency, where n is an integer, before processing said response signal to extract eddy current information or defects in said metallic object.

15. A device for non destructive evaluation of defects in a metallic object by eddy currents, comprising at least one field emitter for emitting at least one alternating electromagnetic field at at least one first frequency fi in the neighbourhood of the metallic object, and at least one magnetoresistive sensor for detecting a response signal constituted by a return electromagnetic field which is re-emitted by eddy currents induced by the alternating electromagnetic field in said metallic object, characterized in that it further comprises:
  driving means for driving said at least one magnetoresistive sensor by a current at a second frequency fc which is different from said first frequency fi, so that said at least one magnetoresistive sensor acts as an in situ modulator,
  detecting means for detecting between the terminals of the magnetoresistive sensor a response signal,
  filtering means for filtering the response signal detected by said at least one magnetoresistive sensor to keep either the frequency sum (fi+fc) of said first and second frequencies or the frequency difference (fi−fc) of said first and second frequencies, and
  processing means for processing said filtered response signal and extract eddy current information on defects in said metallic object.

16. A device according to claim 15, characterized in that said detecting means comprises amplification means, means for detecting reference signals at said at least one first frequency fi and at said second frequency fc, multiplying means for mixing said at least one first frequency fi and said second frequency fc and at least a lock-in amplifier for detecting the frequency sum (fi+fc) of said first and second frequencies or the frequency difference (fi−fc) of said first and second frequencies.

17. A device according to claim 16, characterized in that the magnetoresistive sensor comprises multiple contact points for voltage measurements.

18. A device according to claim 16, characterized in that the magnetoresistive sensor comprises an array of sensors.

19. A device according to claim 16, characterized in that the magnetoresistive sensor is a Hall effect sensor.

20. A device according to claim 16, characterized in that the magnetoresistive sensor is an anisotropic magnetoresistive sensor (AMR), a giant magnetoresistive sensor (GMR), a giant magnetoimpedance sensor (GMI) or a tunnel magnetoresistive sensor (TMR).

21. A device according to claim 15, characterized in that the magnetoresistive sensor comprises multiple contact points for voltage measurements.

22. A device according to claim 15, characterized in that the magnetoresistive sensor comprises an array of sensors.

23. A device according to claim 15, characterized in that the magnetoresistive sensor is a Hall effect sensor.

24. A device according to claim 15, characterized in that the magnetoresistive sensor is an anisotropic magnetoresistive sensor (AMR), a giant magnetoresistive sensor (GMR), a giant magnetoimpedance sensor (GMI) or a tunnel magnetoresistive sensor (TMR).

25. A device according to claim 24, characterized in that the magnetoresistive sensor has a yoke shape, in that the length (L) of the yoke and the length (l) of the lateral arms of the yoke each are at least three times the width (w) of the yoke, and in that the width (w) of the yoke is comprised between 2 µm and 12 µm.

26. A device according to claim 24, characterized in that said at least one field emitter is a planar coil.

27. A device according to claim 15, characterized in that said at least one field emitter is a planar coil.

28. A device according to claim 27, characterized in that the magnetoresistive sensor is built on a very thin silicon substrate.

29. A device according to claim 27, characterized in that the magnetoresistive sensor is built on a bevelled substrate.

30. A device according to claim 27, characterized in that the magnetoresistive sensor is built on a flexible substrate.

31. A device according to claim 15, characterized in that the magnetoresistive sensor is built on a very thin silicon substrate.

32. A device according to claim 15, characterized in that the magnetoresistive sensor is built on a bevelled substrate.

33. A device according to claim 15, characterized in that the magnetoresistive sensor is built on a flexible substrate.

* * * * *